United States Patent
Chirife

[19]

[11] Patent Number: 6,119,040
[45] Date of Patent: Sep. 12, 2000

[54] CARDIAC PACEMAKER UPPER RATE LIMIT CONTROL

[76] Inventor: Raul Chirife, José C. Paz 1277, 1641 Acassuso, Buenos Aires, Argentina

[21] Appl. No.: 09/106,674

[22] Filed: Jun. 29, 1998

[51] Int. Cl.[7] ..................................................... A61N 1/365
[52] U.S. Cl. ............................................................. 607/18
[58] Field of Search ................................................ 607/18

[56] References Cited

U.S. PATENT DOCUMENTS

| | | |
|---|---|---|
| 4,535,774 | 8/1985 | Olson . |
| 4,686,987 | 8/1987 | Salo et al. . |
| 4,708,143 | 11/1987 | Schroeppel . |
| 4,719,921 | 1/1988 | Chirife ....................................... 607/17 |
| 4,733,667 | 3/1988 | Olive et al. ............................... 607/24 |
| 4,773,401 | 9/1988 | Citak et al. . |
| 4,856,524 | 8/1989 | Baker, Jr. . |
| 4,865,036 | 9/1989 | Chirife . |
| 4,873,980 | 10/1989 | Schaldach . |
| 4,919,137 | 4/1990 | Schaldach . |
| 4,926,863 | 5/1990 | Alt . |
| 5,154,171 | 10/1992 | Chirife . |
| 5,156,147 | 10/1992 | Warren et al. ............................ 607/24 |
| 5,168,869 | 12/1992 | Chirife . |
| 5,174,286 | 12/1992 | Chirife . |
| 5,179,949 | 1/1993 | Chirife . |
| 5,562,711 | 10/1996 | Yerich et al. . |

*Primary Examiner*—William E. Kamm
*Attorney, Agent, or Firm*—Ryan Kromholz & Manion, SC

[57] ABSTRACT

Method and apparatus for automatically setting a variable upper rate limit for the pacing pulse signal provided by a rate adaptive implantable pacemaker which relies on a non-physiological sensor to determine the pacing needs of the patient. A physiological parameter of the patient's condition is sensed and used to determine an upper limit for the pacing rate otherwise called for based on the reading of the non-physiological sensor. In a disclosed embodiment, the ventricular preejection period is monitored as the physiological parameter, and the rate of change of this parameter is utilized to set the upper limit of the pacing pulse rate.

11 Claims, 2 Drawing Sheets

CARDIAC PACEMAKER UPPER RATE LIMIT CONTROL

TECHNICAL FIELD

The present invention relates to techniques for sensor-controlled rate adaptive cardiac stimulation, and particularly to methods and apparatus for establishing automatic upper rate limits for rate adaptive pacemakers.

BACKGROUND OF THE INVENTION

Early implantable pacemakers provided stimulus pulses at fixed rates, or within a range of rates that was externally programmable, to restore a normal resting heart rate to a patient suffering bradycardia. Such cardiac stimulation rates may meet the metabolic demand of the patient at rest or in low level exercise, but are generally inadequate to meet the demands of moderate to vigorous exercise. Sensor-controlled implantable cardiac pacemakers have been developed to attempt to adjust the rate of production of pacing pulses to meet metabolic demands, as dictated by the physiological condition of the patient in whom the pacemaker is implanted, utilizing parameters such as blood pH, body temperature, respiration rate, ventricular preejection period (PEP), or body motion or activity, for example. Many such sensor-controlled pacemakers are still inadequate to meet the demands of the patient due to limitations in sensitivity, specificity, and/or speed of response.

The type of rate adaptive pacemaker which relies on determining the activity, or body motion, of the patient to set the stimulus pulse rate has the advantage of the activity sensor being positioned within the case of the pacemaker, and not extending to a part of the patient's body removed from the pacemaker. Generally, an electromechanical sensor is included as part of such a pacemaker, and responds to being moved by producing an electrical signal which the pacemaker signal processing circuitry then interprets. Such an electromechanical sensor may be an accelerometer, positioned within the case of the pacemaker and cushioned from the case to detect acceleration of the body of the patient with the use of an inertial mass and appropriate detectors of movement of the mass. Alternatively, the activity, or motion, sensor may include a piezoelectric crystal attached to the interior of the pacemaker case to detect vibrations of the case, as indicative of movement of the patient's body. If it is determined that the patient's activity has increased, the pacemaker may respond by increasing its pacing pulse rate, in proportion to the sensor signal.

Activity/motion sensors are incorporated into a majority of rate adaptive pacemakers available today because they provide sufficient rate compensation for most conditions, offer fast response time, and are easy to program. However, such sensor-controlled pacemakers may lack specificity, since not all movement detected by an electromechanical sensor is activity by the patient that demands an increased rate of heartbeat. For example, the activity sensor may be detecting motion due to the patient riding in an automobile, or in an elevator. Such circumstances would normally not require an increased heart rate. The activity/motion-controlled pacemaker may not be able to distinguish such movement of the patient from movement associated with the patient exercising, and needing an increased heart rate. As a result, the pacemaker is conditioned to provide an increasing pacing rate at times when the patient may not require such a rate, and which may be harmful under certain clinical conditions. Another example in which the activity sensor response is not in proportion to the patient's activity occurs when the patient is going down stairs. In such a case, an activity sensor-controlled pacemaker generally provides a much greater pacing rate than is actually needed by the patient, since body motion and vibration are more intense going down stairs than, for example, going up stairs, although the latter exercise is the more stressful for the patient.

All rate responsive pacemakers have the capability of being externally programmed for a minimum and a maximum pacing rate, which are generally adjusted according to the patient's age, clinical condition, and the expected level of physical activity. The minimum pacing rate is called Lower Rate and the maximum pacing rate is called Upper Rate. Setting the maximum pacing rate at a relatively low level may offer some protection against excessive pacing rates caused by lack of specificity of the activity sensor, but will deprive the patient of the needed rate under heavy exercise conditions. Other sensors which detect physiological cardiac signals, such as PEP, are more specific to increased metabolic demands, but are less sensitive, sometimes not responding adequately under low level exercise or postural changes.

With rate adaptive pacemakers using non-physiological sensors, such as activity/motion sensors, the possibility exists that the heart will be paced inappropriately fast for the prevailing metabolic demands. It would thus be advantageous and desirable to equip a rate-responsive cardiac pacemaker with a mechanism for setting an automatically variable upper rate limit (URL) for the stimulus signal provided by the pacemaker in response to the signal generated by the activity sensor, wherein the URL is determined by the level of change of a physiological parameter. A large activity-controlled pacing rate increase would thus be allowed only if there is confirmation of a significant increase in metabolic demand, thus increasing the specificity of the rate-adaptive pacemaker, and adding an important safety feature. The present invention provides such method and apparatus.

During cardiac systole, blood pressure in the aorta and pulmonary artery rises until the aortic and pulmonic heart valves close, after which arterial pressure declines during diastole. PEP is the time interval between the beginning of the cardiac cycle, initiated by the QRS complex of the electrocardiogram, or by a pacing pulse, whichever is first to occur and the commencement of ventricular ejection. The QRS complex pulse, or a pacing pulse, causes electrical depolarization of the heart, including, ultimately, depolarization of the ventricles, and ventricular contraction. There is an initial period of ventricular contraction during which muscular contraction occurs but no change occurs in the volume of the ventricles, there is no ejection of blood from the ventricles, and pressure in the ventricles rises. This phase is called isovolumic contraction time (IVCT), and constitutes most of the duration of PEP. During IVCT, pressure within the ventricles rises until the ventricle pressure exceeds the back pressure in the aorta and the pulmonary artery to open their respective heart valves. PEP ends as soon as the aortic and pulmonic valves open and blood flows into the aorta and pulmonary arteries, causing ventricular volume to gradually decrease as blood is emptied into these blood vessels. PEP is thus the time interval between the beginning of the cardiac cycle, marked by the QRS waveform, or by a pacing pulse, whichever is first to occur, and the commencement of ventricular ejection. For a given patient, the IVCT varies with metabolic demands, and, therefore, the PEP varies accordingly.

The duration of the PEP is primarily determined by the speed of contraction of muscle fibers of the myocardium, that is, the myofibrils. The faster the myofibrils contract, the faster the level of back pressure in the aorta and pulmonary arteries will be reached in the ventricle, and the shorter the PEP will be. Therefore, PEP is an indicator of the contraction ability of the heart, or contractility. That is, as contractility increases, PEP shortens. During exercise, or when the body is subject to stress, whether it is mental or physical, there is an increase in tone of the sympathetic nervous system and an increase in release of catecholamines into the blood stream, both of which enhance the metabolic activity of the heart musculature to increase contractility and, concurrently, heart rate, to effect the necessary response to the increased activity or stress. Under stress conditions, it would be expected that heart rate would increase in proportion to PEP shortening, both being guided by the same neuro-hormonal stimulation. During artificial increasing of pacing at rest, however, there is no shortening of PEP. Furthermore, under such conditions, PEP may even tend to lengthen due to reflex hemostatic or hemodynamic factors. Any increase in heart rate not associated with a corresponding shortening of PEP may thus be considered either inadequate or excessive, compared to the needs of the patient under the prevailing conditions.

Although the onset of PEP is unique, being signaled by the onset of electrical depolarization of the ventricles, the end of PEP may be determined in several ways. One technique uses the onset of rise in pulmonary artery or aortic pressure as a signal of the end of ejection. Another method uses Doppler flow indicators to signal the onset of blood passage through the arteries. A third technique measures intraventricular impedance as an indicator of ventricular volume. Intraventricular impedance is known to reciprocally reflect intraventricular blood volume, thus the onset of ventricular impedance increase will also signal the onset of ventricular ejection, that is, the end point of PEP.

Various techniques are known for monitoring intracardiac impedance, generally utilizing two or more electrodes positioned within a heart chamber. For example, my U.S. Pat. No. 4,865,036 discloses measuring intraventricular impedance using three electrodes positioned within the ventricle and an applied high frequency signal, with voltage changes across two of the electrodes detected to monitor the movement of blood into and out of the ventricle. My U.S. Pat. No. 5,154,171 discloses techniques for sensing intracardiac impedance by monitoring the amplitude modulation of the high frequency signal applied across electrodes by changes in the ventricular volume, utilizing two or more electrodes. My U.S. Pat. No. 5,179,949 also discusses impedance measurement whereby a driving signal is delivered to intraventricular electrodes and the resulting voltage is detected from the same electrodes to monitor changes in the blood volume through resulting impedance changes. U.S. Pat. No. 4,686,987 also utilizing two intraventricular electrodes across which an oscillatory signal is applied, and the amplitude modulation of the signal across the same two electrodes, due to changes of the volume of blood in the heart chamber effecting impedance between the electrodes, is analyzed. U.S. Pat. No. 4,773,401 discloses interpreting the intraventricular waveform to determine the end of PEP. U.S. Pat. No. 5,562,711 also discusses using two or more electrodes in sensing intraventricular impedance.

SUMMARY OF THE INVENTION

A cardiac pacemaker according to the present invention incorporates a mechanism that automatically sets URLs for rate-responsive stimulus pacing signals, depending on the physiological requirements of the patient. The present invention provides method and apparatus utilizing a second, physiological sensor to determine whether a first, activity sensor is detecting activity of the patient as opposed to activity in the environment of the patient, and then to establish a safe URL for the pacing signal, depending on the determination of metabolic need. In a particular embodiment, the present invention utilizes the ventricular preejection period (PEP) as a measure of the physiological requirements of the patient to set the URL for the pacing signal, and allows the activity sensor to reach, but not surpass, the URL. Thus, the pacing rate will be commanded based on sensing by the activity/motion sensor, within limits set based on sensing by the physiological sensor.

An implantable rate adaptive cardiac pacemaker comprises a first sensor that is sensitive to a non-physiological parameter, and that provides a first electrical sensor signal that reflects that parameter, and also provides a second sensor that is sensitive to a physiological parameter, and that provides a second electrical sensor signal that reflects that parameter. A pulse generator provides pacing pulse signals to stimulate the heart of the patient, and electrodes apply the pacing pulse signals to the heart. Control circuitry includes apparatus that produces command signals to the pulse generator, that determines the rate of pacing pulse signals based on information received from the first electrical sensor signal, subject to upper rate limits selected based on information received from the second electrical sensor signal.

A pacemaker according to the present invention may also include electrocardiogram circuitry that monitors the electrocardiogram of the patient to detect QRS complex pulses. The second sensor may include apparatus that is sensitive to the PEP. Further, the second sensor may comprise circuitry that detects ventricular impedance, and measures the PEP. The present invention may include circuitry that determines the rate of change of the PEP, and further determines URLs based on that rate of change. Control circuitry of the present invention compares information from the first electrical sensor signal with the determined URL and sets the rate for the pacing pulse signal based on the comparison.

In a method of the invention, pacing pulse signals are provided to the heart of a patient, utilizing a rate responsive cardiac pacemaker having a pacing pulse generator, electrodes that apply pacing pulse signals to the heart, and apparatus that monitors the electrocardiogram, by monitoring a non-physiological parameter utilizing a first sensor that provides a first electrical sensor signal that reflects that parameter, monitoring a physiological parameter utilizing a second sensor that provides a second electrical sensor signal that reflects that parameter, processing the sensor signals, determining the rate for a pacing pulse signal based on information received from the first sensor signal, determining a URL for the rate of the pacing pulse signal based on information received from the second sensor signal, and producing and communicating a command signal to provide a pacing pulse signal at a rate based on the information from the first sensor signal, subject to a URL selected based on the information from the second sensor signal.

Processing the second electrical sensor signal may include measuring the PEP of the cardiac cycle, and determining the rate of change of the PEP. Monitoring the physiological parameter may include monitoring electrical impedance within a ventricle of the heart.

The present invention, in the embodiment illustrated herein, provides a second, physiological sensor to measure PEP, and determines the rate of change in PEP, to control the upper rate of the pacemaker. Thus, the maximum pacing rate allowed by the pacemaker, that is, the URL, will be determined by the change in PEP, and particularly by the rate of change of PEP.

DETAILED DESCRIPTION OF THE PREFERRED EMBODIMENT

Figure 1:
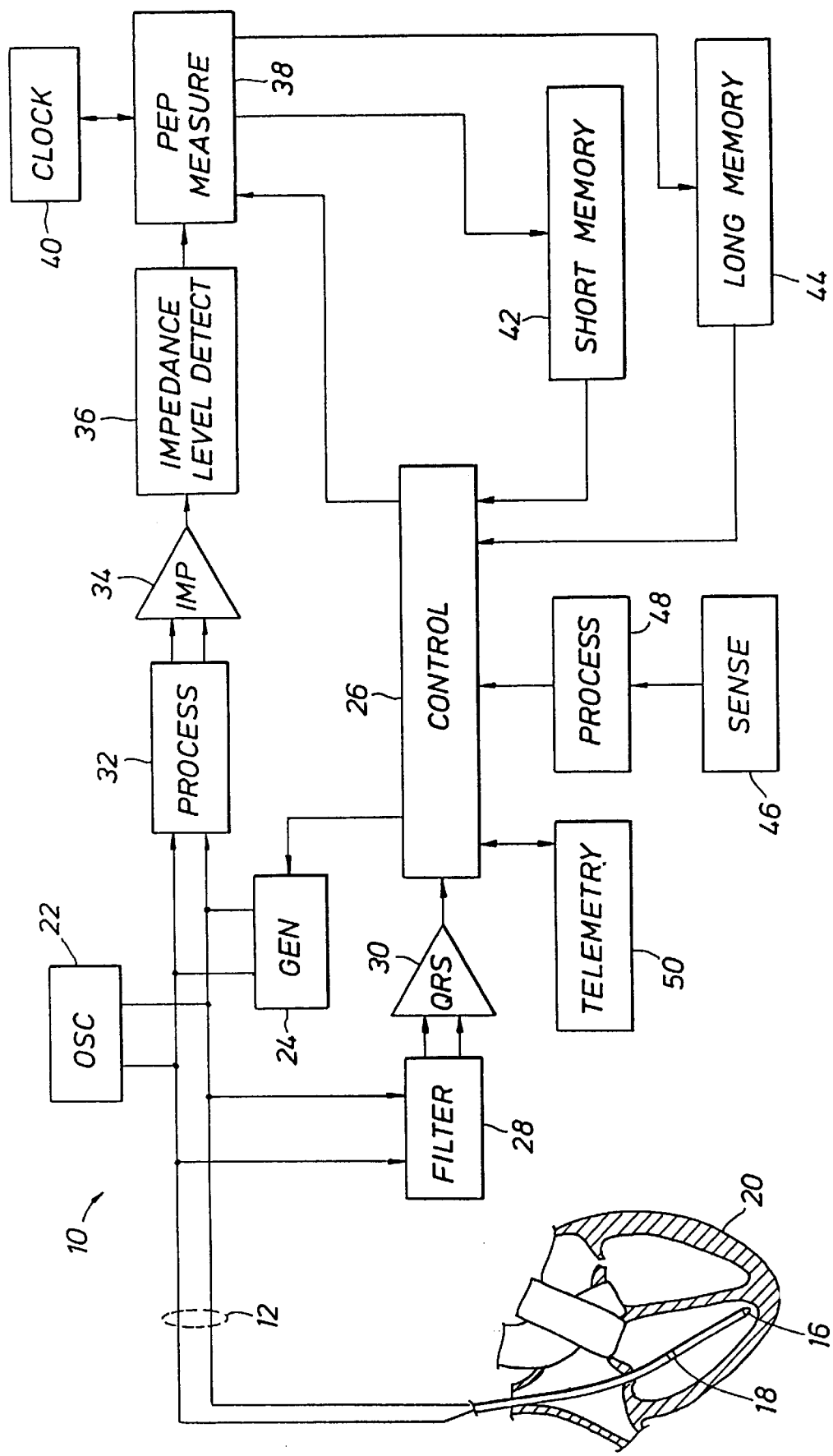
FIG. 1 is a block diagram of an implantable cardiac pacemaker incorporating an upper rate limit control according to the present invention.

A block diagram of an implantable rate-responsive cardiac stimulator, or pacemaker, utilizing a determination of the PEP to limit the maximum pacing rate of the pacemaker according to the present invention, is shown generally at 10 in FIG. 1. For purposes of illustration and discussion, and not for limitation, the stimulator 10 may be considered to operate in demand, single chamber mode. Further, for purposes of clarity, some details of pacemakers, known in the art, have not been drawn expressly in the illustration of the pacemaker 10. As noted above, PEP may be determined in various ways. The embodiment of the present invention illustrated in FIG. 1 determines the PEP by monitoring intracardiac impedance, which can also be accomplished by using various techniques, as noted above.

A bipolar lead 12 carries two electrodes 16 and 18, positioned in the right ventricle of the patient's heart, which is shown schematically at 20, with the distal electrode 16 at the apex of the ventricle, and the proximal electrode 18 being a ring positioned at a higher location. A constant current carrier oscillator 22 produces a high frequence ac or square wave signal across the electrodes 16 and 18 by way of the lead 12. The frequency of the waveform from the oscillator 22 is typically in the range from 250 Hz and above, and is sufficiently high to resolve the impedance waveform from one to four msec.

A variable rate stimulus pulse generator 24 is also connected across the electrodes 16 and 18 by way of the bipolar lead 12. The pulse generator 24 produces a pulse signal for stimulating the beat of the heart 20, under a command from a microprocessor, or control circuit 26. Alternatively, a separate set of leads (not shown) may extend from the generator 24 to other cavities of the heart, such as the atria, to effect the dual-chamber mode of stimulation.

The microprocessor 26 monitors the intracardiac electrocardiogram signal received from the heart at the electrodes 16 and 18, utilizing QRS detection circuitry including a filter 28 and a QRS amplifier 30. The filter 28 is connected across the bipolar lead 12 to receive the electrocardiogram signal and to remove the high frequency signals from the carrier oscillator 22 as well as extraneous noise. The filtered electrocardiogram signal is amplified by the QRS amplifier 30, and communicated to the microprocessor 26. Thus, the pacemaker 10 senses the QRS complex pulse for operation in the demand mode, and also for calculating the length of the PEP, as further discussed below. In the event that a pacing pulse occurs before the QRS complex to initiate a cardiac cycle, the detection circuitry including the filter 28 and the amplifier 30 will detect the pacing pulse for use in calculating the length of the PEP. Again, a separate set of electrodes (not shown) can be dedicated to sensing the electrocardiogram as an alternative to using the illustrated electrodes 16 and 18. Further, the metallic case (not shown) of the pacemaker 10 may be utilized as an electrode, positioned away from the heart.

In the embodiment illustrated, to sense changes in a physiological parameter of the patient, namely, the PEP, signal processing circuitry 32 is provided to receive and detect the high frequency carrier signal impressed on the lead 12 by the oscillator 22, as modulated by changes in the impedance within the blood volume of the right ventricle between the electrodes 16 and 18. The amplitude modulation of the signal from the oscillator 22 is proportional to the instantaneous impedance across the electrodes 16 and 18. Since intraventricular impedance is inversely proportional to intraventricular volume, a brisk impedance rise detected between the electrodes 16 and 18 within the right ventricle is an indication of the onset of ejection, that is, a reduction of right ventricular volume due to the emptying of blood into the pulmonary artery. Output from the processor 32 is conducted to a sense amplifier 34, and the amplified signal is conducted to an impedance level detector 36, which detects a sudden increase in the intraventricular impedance as an indication of the onset of ejection, that is, the end point of PEP.

The impedance level detector 36 may, for example, demodulate the modulated carrier signal from the sense amplifier 34 to remove the carrier signal, after which the time-varying impedance waveform envelope reflecting the instantaneous ventricular impedance is analyzed for changes in the impedance. When, during the cardiac cycle, the amount of blood contained in the ventricle reaches a maximum, the impedance is at a minimum, and this fact is detected in the demodulated signal in the level detector 36. As soon as rising muscle tension due to ventricular systole increases the pressure of the blood in the ventricle sufficiently to open the pulmonic valve and initiate ejection, the impedance between the two electrodes 16 and 18 in the ventricle rises sharply. The end of the PEP is thus detected in the level detector 36 by the voltage level of the impedance signal waveform rising above a predetermined value coincident with the onset of blood flow out of the ventricle. For example, an increase to 25% above the minimum value of the ventricle impedance may be used to mark the end of the PEP. Other methods may be used to analyze the impedance waveform in the impedance level detector 36 to mark the end of the PEP. Whatever analysis is carried out on the impedance waveform, the impedance level detector 36 produces a trigger signal, output to a PEP measuring circuit 38, signaling the end of the PEP.

The PEP measuring circuit 38 also receives a trigger signal from the control circuit 26, signaling the start of a cardiac cycle with a QRS complex pulse, or a pacing pulse, in the electrocardiogram signal, as detected and communicated to the control circuit by way of the electrodes 16 and 18, the lead 12, the filter 28, and the amplifier 30, as discussed above. A clock circuit 40 is provided whereby the PEP measuring circuit 38 measures the time lapse between the beginning of the cardiac cycle, marked by the trigger signal from the control circuit 26, and the end of the PEP, marked by the trigger signal from the impedance level detector 36. This measured time value between the two trigger signals corresponds to the length of the PEP.

For each cardiac cycle, the electrocardiogram signal is monitored, and the start of the cycle caused by the occurrence of a QRS complex or of a pacing pulse, whichever is first to occur, is detected, and a trigger signal is produced by the control circuit 26 and communicated to the PEP measuring circuit 38 to mark the beginning of the cycle; also, for each cardiac cycle, the intraventricular impedance is monitored and the end of the PEP, characterized by a sudden increase in impedance value, is detected, and a trigger signal is produced by the impedance level detector 36 and communicated to the PEP measuring circuit to mark the end of the PEP. The clock 40 is started by the trigger signal marking the start of the cardiac cycle, and is stopped by the trigger signal marking the end of the PEP. The PEP measuring circuit measures the time lapse between the starting and the stopping of the clock 40, and produces a signal, such as a voltage level signal, proportional to the lapsed time measured. Each such time lapse signal thus reflects the duration of the PEP of the corresponding cardiac cycle.

The PEP duration measurements determined by the PEP measuring circuit 38 are communicated, by way of the time lapse signals, to two memories 42 and 44 in the form of a short term moving average register, and a long term moving average register, respectively. Each of the memories 42 and 44 performs an average process of the time lapse signals input to the respective memory from the PEP measuring circuit 38, for a number of time lapse signals designated for the respective memory. For each such averaging process, the respective memory 42 or 44 produces an output signal, which may be in the form of a voltage level signal, reflecting the value of the average determined. It will be appreciated that each time lapse signal communicated to the memories 42 and 44 represents one cardiac cycle, or beat. Typically, the short term register 42 may average the PEP over a period on the order of thirty to sixty beats, or cardiac cycles, and the long term register 44 averages the PEP over a longer period, say, in excess of several hundred beats, or cardiac cycles. The short term register 42 thus produces a series of output signals with each such signal reflecting the average of the PEP, determined over the relatively low number of cardiac cycles designated for that memory, and the long term register 42 thus produces a series of output signals with each such signal reflecting the average of the PEP, determined over the relatively high number of cardiac cycles designated for that memory. Output signals from the registers 42 and 44 are communicated to the control microprocessor 26 for determination of the time rate of change of the PEP, as discussed below.

An activity, or motion, sensor 46 is positioned within the case (not shown) of the pacemaker 10, and produces an electrical output signal depending on movement as determined by the sensor. The activity sensor 46 may be any appropriate motion sensor, such as an accelerometer or a piezoelectric device, for example. In any case, the activity sensor 46 produces an electrical output signal that reflects movement of the sensor and, therefore, movement experienced by the patient. The signal thus generated by the activity sensor 46 is communicated to signal processing circuitry 48, which removes noise from the signal and otherwise processes the signal, which is then communicated to the control microprocessor 26.

Telemetry circuitry 50, including an appropriate antenna circuit (not shown), is connected to the control circuit 26, and provides a mechanism by which data concerning the condition of the pacemaker 10 may be communicated to an appropriate telemetry system (not shown) external to the patient, and by which commands may be communicated to the pacemaker by medical personnel, for example.

In operation, the pacemaker 10 uses a first, activity sensor 46 to detect movement of the patient, and also monitors the PEP through a second, physiological sensor, including the electrodes 16 and 18, and the carrier oscillator 22. A pacing signal is provided to stimulate the patient's heart, if needed, wherein the pulse rate of the pacing signal is determined based on the movement of the patient, as detected by the first sensor 46, and is limited in upper value based on the change in PEP, if any. A change in the heart rate due to a physiological event, such as an increase in contractility of the ventricle accompanying an increase in physical activity of the patient, will be accompanied by a shortening of the PEP. The rate of the pacing pulses available from the pacemaker 10 will increase in proportion to the signal arising from the activity sensor 46. However, if the activity sensor 46 detects an increase in movement without the physiological sensor detecting a corresponding shortening in PEP, the conclusion is that the patient activity has not increased, and that no physiological event has taken place requiring a heart rate faster than a predetermined default activity upper rate. The microprocessor 26 uses the information concerning the PEP to place a corresponding upper limit on the rate of pacing signal that will be ordered from the pulse generator 24. More specifically, the rate of change of PEP is determined, and a range of PEP change over time is considered for so limiting the upper pacing signal rate.

In particular, the pacing signal generator 24 is provided to produce a stimulus pulse signal that is conveyed to the heart by the lead 12, and the electrodes 16 and 18. The pacing signal is produced by the generator 24 in response to a command signal from the control multiprocessor 26. Some features of the pacing signal provided by the pacing generator 24, including pulse height, or voltage, and duration, are programmed into the microprocessor 26, and can be selectively altered using the telemetry circuitry 50. The rate of the pacing signal to be produced by the pacing generator 24 is determined by the microprocessor 26 in response to the activity signal from the motion sensor 46, subject to the URL as determined based on the rate of change of the PEP determined in the microprocessor using measurement information from the memories 42 and 44. The command from the control circuit 26 to the pacing generator 24 dictates the specifics of the pacing signal to be produced, including pulse height, pulse width, and pulse rate, among other signal parameters. If the activity sensor 46 does not detect movement of the patient, then the process of measuring the PEP is ineffective, and the rate of the pacing signal commanded to be produced by the pacing signal generator 24 is a default rate, such as an at-rest rate, that is, a rate adequate to supply the patient's pulse rate needs while at rest, regardless of the value of PEP.

The rate of change of the PEP is determined using measurements of the PEP as reflected in signals output from the PEP measuring circuitry 38, and communicated to the short and long term averaging registers 42 and 44, respectively. The short term moving average register 42 averages the PEP values from the most recent measurements, and the long term moving average register 44 averages the PEP values going back over a relatively long period. The microprocessor 26 carries out the process steps, indicated generally at 60 in FIG. 2, using the PEP measurements ultimately to set a URL on the pacing signal, if needed. Thus, in FIG. 2, the short term average PEP value is received by the microprocessor 26 from the short term memory 42 at 62, and the long term average PEP value is received by the microprocessor from the long term memory 44 at 64. The control microprocessor 26 compares the calculated average values of the PEP received at 62 and 64 from the two registers 42 and 44, respectively, that is, the microprocessor calculates the ratio of the short term average, S, to the long term average, L, at 66. Generally, the ratio S/L is a measure of the change in PEP from the PEP at rest. Decisions are made at steps 68, 70, 72 and 74 based on the S/L ratio. The four inequalities 68–74 in FIG. 2 correspond to maximum S/L as follows, where Δ means S/L as a measure of the change in PEP over the period of the number of beats for which an average is calculated by the short term memory 42.

At 68, Δ<0.7=>30% decrease in PEP.(1)
At 70, Δ<0.75=>25% decrease in PEP(2)
At 72, Δ<0.8=>20% decrease in PEP (3)
At 74, Δ<0.9=>10% decrease in PEP (4)

The S/L is used to set the URL, which is the maximum beats/minute (bpm) of the pacing signal that will be commanded by the microprocessor 26 to be produced by the pulse generator 24 in response to the need indicated by the signal from the activity sensor 46.

An upper rate limit is placed on the pacing signal output of the pacemaker 10 depending on the percentage change in the PEP. The URL will be set higher for greater changes in the PEP. Thus, a "yes" answer at 68 indicates that the PEP has decreased by more than 30%, and the URL is set at 150 bpm, as noted at 76. A "no" answer at 68 indicates that the PEP has decreased by 30% or less, and a decision is made at 70. A "yes" at 70 indicates that the PEP has decreased by more than 25%, but no more than 30% (from the decision at 68), and the URL is set at 130 bpm, as noted at 78. A "no" at 70 indicates that the PEP has decreased by 25% or less, and a decision is made at 72. A "yes" at 72 indicates that PEP has decreased by more than 20%, but no more than 25% (from the decision at 70), and the URL is set at 110 bpm, as noted at 80. A "no" at 72 indicates that the PEP has decreased by 20% or less, and a decision is made at 74. A "yes" at 74 indicates that the PEP has decreased by more than 10%, but no more than 20% (from the decision at 72), and the URL is set at 90 bpm, as noted at 82. A "no" at 74 indicates that the PEP has decreased by 10% or less. In that case, the control circuit 26, at 84, allows an increase in the rate of the pacing signal from the pulse generator 24, as determined based on the activity sensor signal, to no more than a programmed default value, generally less than 100 bpm, regardless of how much greater than that the activity sensor signal determines the pacing rate should be.

Figure 2:
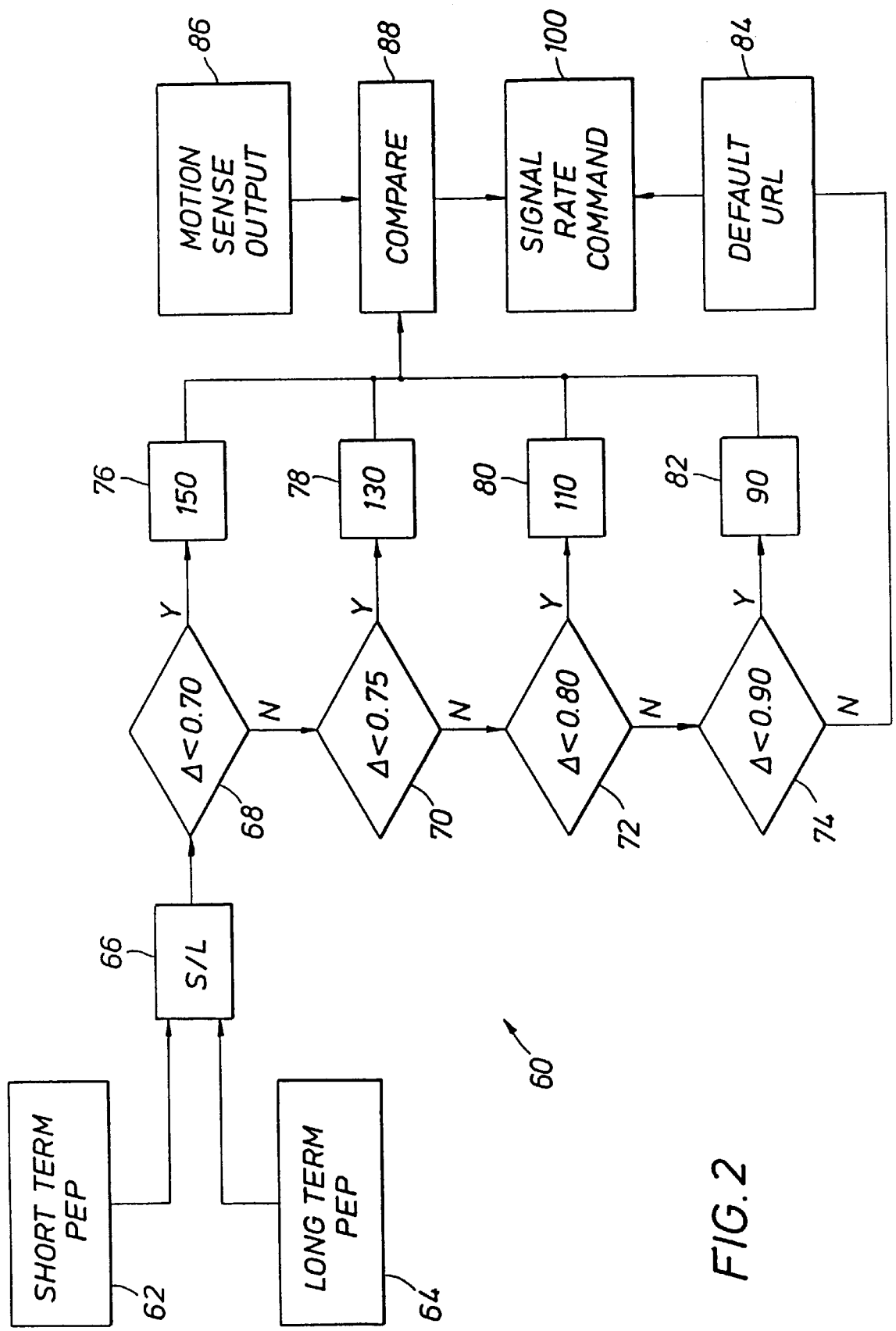
FIG. 2 is a functional flowchart of process steps for implementing an upper rate limit control according to the present invention.

The microprocessor 26 receives the processed activity sensor signal at 86 in FIG. 2. If the default URL has not been imposed at 84, the pacing signal rate that would be required, based only on the processed activity sensor signal, is compared at 88 with the URL as set at 76–82, based on the rate of change of the PEP as reflected in the determination of S/L. The activity sensor signal may indicate the need for a fast rate pacing signal, but the S/L calculation tells whether there is a concurrent indication of an actual need for such a high rate pacing signal, based on the physiological condition of the patient. The S/L measurement can thus determine a "false positive" activity sensor condition and limit the pacing rate indicated based on information from the activity sensor signal. The microprocessor 26 compares the URL with the need as indicated by the activity sensor signal, and allows only pacing rates that are no higher than the prevailing URL, and, in the case of a "no" at 74, allows only the default URL.

Thus, for the case of an activity sensor signal indicating motion, the microprocessor 26 provides command signals at 100 to the pulse generator 24, as needed, specifying the default rate as determined at 84 due to "no" answers at all inquiries 68–74, or, in the case of a "yes" answer at one of the inquiries, and after the comparison at 88, specifying the rate called for based on the information from the activity sensor signal, up to but not exceeding the URL set at 76–82.

It will be appreciated that the URL values shown in 76–82, as well as the default value at 84, of FIG. 2 can be set at other values, and that the number of inquiries, such as 68–74, may be increased or decreased. Also, the threshold percentages of change of PEP included in the inquiries, such as 68–74, may be set at other values. Further, the present invention may be incorporated in other types of pacemakers using non-physiological sensors other than activity, or motion, sensors to command the pacing rate.

The use and operation of the pacemaker 10 as illustrated in FIGS. 1 and 2 may be further appreciated by considering some examples. If the activity sensor 46 does not detect motion, then no signal, reflecting motion, is produced, and, in the event that a QRS complex pulse is not detected in the electrocardiogram signal, monitored across the ventricle electrodes 16 and 18, and communicated, by way of the filter 28 and the QRS amplifier 30, to the control circuit 26 before a predetermined time lapse since the last QRS, or pacing, pulse has been detected, the pacing generator 24 will be commanded by the control circuit to pace the heart at the default rest rate. If, on the other hand, the activity sensor 46 detects some amount, or degree, of movement, and produces an activity sensor signal accordingly, the motion signal is processed by the processing circuitry 48, and the processed signal is communicated to the microprocessor 26, as indicated at 86.

As an example of motion detected, consider that the extent of movement detected by the activity sensor 46 would require a cardiac pacing rate of 120 bpm. Without the improvements of the present invention, the microprocessor 26 would command that the pulsing signal generator 24 provide a pacing signal at the rate of 120 bpm regardless of the source or nature of the movement detected by the activity sensor 46, which movement could be true physical activity by the patient, or passive motion of the patient.

With the present invention, the PEP is continuously monitored and measured, so that the pacemaker 10 is apprised of the physiological condition of the patient in addition to any information obtained from the activity sensor 46 indicating detected motion. Thus, a carrier signal from the carrier oscillator 22 is impressed across the electrodes 16 and 18, and variation in the impedance within the right ventricle of the heart 20 modulates the carrier signal, which is communicated to the processing circuitry 32. The output from the processor 32 is amplified at 34, and communicated to the impedance level detector 36 which transmits a trigger signal to the PEP measuring circuit 38 marking the end of each PEP. Meanwhile, the electrocardiogram signal across the ventricle electrodes 16 and 18 is monitored, and for each QRS complex pulse, or pacing pulse, detected, using the filter 28 and the QRS amplifier 30, the control circuit 26 transmits a trigger signal to the PEP measuring circuit 38 marking the beginning of a cardiac cycle. Utilizing the clock circuit 40, the PEP measuring circuit 38 measures the time lapse between each trigger signal from the control circuit 26, marking the beginning of a cardiac cycle, and the next trigger signal from the impedance level detector 36, marking the end of the corresponding PEP, to produce a PEP time lapse signal for each cardiac cycle. The PEP measuring circuit 38 thus produces a continuous stream of PEP time lapse signals, reflecting the duration of the PEP of succeeding cardiac cycles, and communicates these signals to the two moving average register memories, 42 and 44.

Measurements of PEP values for short term and long term periods are stored, then averaged, in the short term averaging register 42 and in the long term averaging register 44, respectively, and the resulting averages communicated to the control circuit 26 at 62 and 64, as shown in FIG. 2. If the control circuit 26 received an activity sensor signal, indicating that motion has been detected, the calculation of S/L is performed at 66, and the result tested at the inquiries 68–74. Otherwise, if the activity sensor 46 does not detect motion, so that the control circuit 26 does not receive a motion signal, the processing of PEP time lapse signals need not proceed to the calculation of the S/L ratio at 66.

For the above example in which the activity sensor 46 detects motion and produces a signal calling for a pacing rate of 120 bpm, consider that the patient is moving quickly downstairs. This exercise causes a considerable amount of body motion and vibration, but a minimal increase in metabolic demands. The movement detected by the activity sensor 46 is substantial, while the extent of metabolic activity change detected by monitoring the PEP is slight, requiring minimal change in heart rate. The change in PEP caused by the exercise results in the S/L calculated at 66 to be 0.78. The method then determines "no" answers at 68 and 70, and a "yes" answer at 72. The microprocessor 26 then sets a URL on the pacing signal to be commanded of 110 bpm, as required at 80. The microprocessor 26 compares the 120 bpm requested, based on the activity sensor signal, with the 110 bpm URL, based on the calculated S/L value of 0.78, at 88. Then, at 100, the microprocessor 26 provides a command to the pacing generator 24 for a pacing pulse, as needed, at a rate up to but not more than the URL of 110 bpm. Thus, the patient will not be subjected to a pacing signal at a rate in excess of a safe limit determined by monitoring the PEP.

For another example of motion detected, consider that the activity sensor 46 detects motion and produces a signal calling for a pacing rate of 125 bpm, and that the movement detected by the activity sensor is due entirely to vigorous exercise by the patient. In this case, the PEP decreases to a greater extent due to a greater influx of catecholamines into the bloodstream and increased stimulation of the heart by the adrenergic nervous system, and at a faster rate. This change in the PEP is reflected in a smaller magnitude for the value of S/L calculated at 66, say, 0.72. Then, the method determines a "no" answer at 68, but a "yes" answer at 70, setting the URL at 130 bpm, as noted at 78. Comparison of this URL with the 125 bpm pacing rate requested based on the activity sensor signal at 88 results in the microprocessor 26 commanding a pacing signal at 100, as needed, at the full 125 bpm rate.

For yet another example of motion detected, consider that the activity sensor 46 detects motion and produces a signal calling for a pacing rate of 130 bpm, and that the movement detected by the activity sensor is due to the patient being transported in a moving vehicle, with the patient otherwise at rest. In this case, the PEP exhibits little change with time. This minimal change in the PEP is reflected in a value of S/L calculated at 56 of, say, 0.95. Then, the method determines "no" answers at all inquiries 68–74, and imposes the default URL at 84 on any command from the control circuit 26 to the pacing generator 24 at 100 so that the heart receives pacing pulses, as needed, not in excess of the default pacing rate. In this case, no comparison takes place at 88.

As illustrated by the examples, the present invention effectively determines whether the non-physiological sensor of a rate responsive pacemaker is detecting the condition of the patient, or detecting something in the environment of the patient, and establishes an upper rate limit on the pacemaker as needed to insure that the patient will not be given a too fast, unsafe pacing rate for the patient's condition. Thus, for rates below a predetermined, safe, upper rate, the activity sensor controls fluctuations in the pacing rate, but, for faster pacing rates, validation is needed from a second, physiological sensor, monitoring the PEP, for example. Further, if no motion signal is generated by the non-physiological sensor, the process for determining a URL for pacing signals can be aborted.

Sensing a physiological parameter other than the PEP may be employed as part of the present invention. Further, the physiological parameter sensed, such as the PEP, as in the illustrated embodiment, can be measured in any appropriate manner that will provide the information for determining the change in the parameter, utilizing any circuitry and electrodes appropriate.

The present invention would be beneficial in cases where pacemakers with non-physiological sensors are used to obtain data to adjust the pacing rate. Such sensors provide sensing signals to so adjust the pacing rate independently from the physiological demands of the patient, and with no feedback. An upper rate limit might be set for such pacemakers, without the present invention, based on a doctor's judgment, or the results of a treadmill test. However, such criteria for setting an upper rate limit for a pacing signal are not representative of the type of experience most patients normally have in daily life, and can result in patients frequently being paced at too rapid a rate. The present invention sets a variable upper rate limit in accordance with the physiological demand of the patient, using a physiological sensor. Further, in general, pacemakers relying on only non-physiological sensors to determine the rate of pacing pulses may be modified, for example, to include the present invention.

The foregoing disclosure and description of the invention is illustrative and explanatory thereof, and various changes in the method steps as well as the details of the apparatus may be made within the scope of the appended claims without departing from the spirit of the invention.

I claim:

1. A rate adaptive cardiac pacemaker, implantable in a patient, comprising:

apparatus comprising a first sensor operative to sense a non-physiological parameter of the condition of the patient and to provide a first electric signal representative of the non-physiological parameter;

apparatus comprising a second sensor operative to sense a physiological parameter of the condition of the patient and to provide a second electric signal representative of the physiological parameter;

a pacing pulse signal generator;

electrodes that receive the pacing pulse signals from the pulse generator and apply them to the heart of the patient for stimulating the heart;

short term averaging circuitry that receives physiological signals representative of successive measures of physiological signals and averages them over a short term;

long term averaging circuitry that receives physiological signals representative of successive measures of physiological signals and averages them over a term longer than said short term; and calculating circuitry that determines the ratio of the average of the measures of physiological signals over the short term to the average of the measures of physiological signals over the long term to produce a result that represents the rate of change of the physiological signals;

apparatus comprising control circuitry that produces command signals that command the pulse generator to provide pacing pulse signals, that determines the rate of the pacing pulse signals so commanded based on information received from the first electric sensor signal, and that so determines the rate of the pacing pulse signals subject to upper rate limits selected based on information received from the calculating circuitry.

2. A pacemaker according to claim 1, wherein said short term averaging circuitry receives signals representative of the lengths of successive preejection periods and averages them over a short term;

long term averaging circuitry that receives signals representative of the lengths of successive preejection periods and averages them over a term longer than said short term; and calculating circuitry that determines the ratio of the average of the preejection periods over the short term to the average of the preejection periods over the long term to produce a result that represents the rate of change of the preejection period.

3. A pacemaker according to claim 2 wherein said calculating circuitry determines upper rate limits for pacing pulse signals based on the rate of change of the preejection period.

4. A pacemaker according to claim 3 wherein said circuitry compares information from the first sensor electric signal with the determined upper rate limit for a pacing pulse signal and sets the rate for pacing pulse signal based on the comparison.

5. A body implantable rate adaptable cardiac pacemaker comprising:

a demand-type artificial heart stimulus pulse generator and electrodes for applying generated artificial stimulus signals to the heart for stimulating the heart to beat on demand;

an electrocardiograph device operative to detect occurrence on the heart of natural QRS heart beat stimulus signals and artificial stimulus signals during each heart cycle, detection of either of the stimulus signals indicating the start of the heart preejection period (PEP), a programable controller having an input for detected stimulus signals, a device for detecting substantially the beginning of ejection of blood from a ventricle of the heart during each heart cycle and for producing a corresponding signal that indicates the end of the PEP, a PEP duration measuring circuit having an input for a signal representing the start of each PEP and an input for the signal that indicates the end of the PEP and the circuit outputs duration signals representative of the durations of successive PEPs, a first memory device operative to store and determine the average of the PEP duration signals over one interval and a second memory device operative to store PEP duration signals and determine the average of the PEP signals over an interval that is longer than the one interval, said controller operating to periodically take the ratio of the average of the one and the longer intervals to produce a signal representative of the rate of change of the PEP, the controller operating to set the upper limit of the artificial stimulus pulse generator stimulus rate to change inversely with the rate of change of the PEP, a motion sensor operating to sense motion of the body in which the pacemaker is implanted and to supply a signal indicative of motion being sensed to the controller, the controller responding by setting the upper limit of the artificial stimulus pulse if motion is sensed concurrently with a decrease in the PEP.

6. A pacemaker according to claim 5 wherein said PEP duration measuring circuit comprises circuitry for sensing the ventricular impedance of the heart and for developing a signal corresponding to substantially the highest impedance occurring in each heart cycle, said signal being indicative of the end of the PEP.

7. A pacemaker according to claim 6 wherein said circuitry for sensing the ventricular impedance includes:

an oscillator having an output coupled to the electrodes for applying a carrier frequency signal to the heart for impedance variations to modulate the carrier, and circuitry for demodulating the carrier to yield a signal representative of the impedance level of the heart.

8. A pacemaker according to claim 6 wherein said motion sensor is a piezoelectric device.

9. A pacemaker according to claim 5 wherein said motion sensor is comprised of an accelerometer.

10. A pacemaker according to claim 5 including circuitry operative to determine the rate of change of the PEP in a succession of heart cycles, said circuitry comprising a short interval averaging circuit having an input for signals representative of the lengths of successive PEPs over a predetermined interval and averages them, a long interval averaging circuit having an input for signals representative of the lengths of successive PEPs over an interval that is longer than said predetermined interval and averages them, and the controller determining the ratio of the averages of the successive PEPs to produce a resulting signal that represents the rate of change of the PEPs.

11. A pacemaker according to claim 10 wherein said resulting signal is coupled to the heart stimulus pulse generator for controlling the upper pulse rate limit of the generator.

* * * * *